United States Patent [19]
Funk et al.

[11] Patent Number: 5,702,588
[45] Date of Patent: Dec. 30, 1997

[54] SOAP FIBER EXTRACTION PROCESS

[75] Inventors: Michael R. Funk, Butler, Pa.; Larry E. Irwin, Overland Park; Michael D. Foster, Mission Hills, both of Kans.

[73] Assignee: Semtech, Inc., Shawnee Mission, Kans.

[21] Appl. No.: 710,864

[22] Filed: Sep. 23, 1996

[51] Int. Cl.$^6$ ............ C10M 177/00; G01N 11/00
[52] U.S. Cl. .......... 205/695; 205/696; 204/450; 204/513; 204/514; 204/553; 252/41
[58] Field of Search .................. 205/695, 696; 204/450, 513, 514, 553; 252/41

[56] References Cited

U.S. PATENT DOCUMENTS

| | | | |
|---|---|---|---|
| 4,444,669 | 4/1984 | Wittse, Jr. et al. | 252/41 |
| 4,728,403 | 3/1988 | Renzler | 205/695 |
| 5,583,284 | 12/1996 | Martin et al. | 75/54.09 |

*Primary Examiner*—Arun S. Phasge
*Attorney, Agent, or Firm*—Chase & Yakimo

[57] ABSTRACT

A method of separating soap fibers from the liquid phase component of grease to prepare the fibers for microscopic analysis includes the steps of admixing a sample of the grease with a solvent to remove the liquid phase component from the fibers and provide a final liquid product having the fibers in suspension therein, contacting the final product with a pair of spaced electrodes, applying a direct voltage across the electrodes to charge the same positive and negative respectively, and withdrawing for analysis a small quantity of the final product from a region thereof proximate the negative electrode after the voltage has been applied for a predetermined energization period. The withdrawn quantity may be deposited on a polished carbon stub and further prepared for analysis by a scanning electron microscope.

7 Claims, 2 Drawing Sheets

SOAP FIBER EXTRACTION PROCESS

FIELD OF THE INVENTION

This invention relates to a method of separating soap fibers from the liquid phase component of grease to prepare the fibers for microscopic analysis and, more specifically, to the extraction of individual soap fibers by the application of an electromotive force to a liquid/fiber suspension.

BACKGROUND OF THE INVENTION

Lubricating greases were originally made of solid fats, such as animal fat. The development of new, more advanced technologies led to lubrication research and the development of metallic and petroleum-based greases that have improved lubricating properties.

One important property of greases today is proper consistency. Grease should be firm enough to retain its shape under its own weight and soft enough to flow under low stress. Modern greases have thus developed and typically comprise a liquid and a solid phase component. The liquid phase component is usually oil and the solid phase component is a thickener or soap, typically metallic soaps of fatty acids which contain positive ions.

Such soap thickened greases are commonly produced by dispersing the soap thickener into the oil at an elevated temperature and allowing the mixture to cool. During the cooling process, the soap component crystallizes to form fibers. This network of soap fibers holds the oil by interfacial and surface forces.

Lithium grease is an example of a common soap thickened grease. Its proper consistency is achieved by milling the cooled mixture to introduce shear forces to the mixture. The shear forces twist and break down the size and shape of the soap fibers. This change in the morphology of the fibers has a direct effect on the forces responsible for holding the liquid and solid phases together. Too much milling may produce a worn out grease or one that exhibits "bleeding-out," which occurs when the chemical and physical forces holding the oil to the soap fibers are no longer sufficient for a complete bond. Examination of the physical characteristics of the fibers is, therefore, necessary if the milling process is to be monitored and evaluated.

Accordingly, a process or method of analyzing and measuring distances, areas, inclusions, length and diameter and other relevant data with respect to soap fibers in grease is desirable. Such analysis would help optimize grease consistency and thus quantify the milling process and prevent bleeding-out. Prior methods employing electron microscopy have produced limited data because the fibers were tangled, even under high magnification, making measurement and analysis difficult.

SUMMARY OF THE INVENTION

Accordingly, a primary object of the present invention is to provide a method of separating soap fibers from the liquid phase component of grease to prepare individual fibers for microscopic analysis.

Another object of the present invention is to provide a method of imaging and quantifying soap fibers in grease.

Yet another object of the present invention is to extract, image and quantify soap fibers of grease through electrophoresis.

A further object of the invention is to provide such a method of separating soap fibers in grease that does not physically alter the fibers.

Still a further object of this invention is to provide a method of testing and evaluating the composition of grease in order to improve quality and facilitate further technological development.

These objects are attained by providing a method of separating soap fibers from the liquid phase component of grease to prepare the fibers for microscopic analysis, comprising the steps of admixing a sample of the grease with a solvent to remove the liquid phase component from the fibers and provide a final liquid product having the fibers in suspension therein, contacting the final product with a pair of spaced electrodes, applying an electromotive force to the electrodes to charge the same positive and negative respectively, and withdrawing for analysis a small quantity of the final product from a region thereof proximate the negative electrode, after the electromotive force has been applied for a predetermined energization period. The method may further comprise an additional step of depositing the withdrawn quantity on a conductive support for viewing by an electron microscope after evaporation of the solvent.

Other objects and advantages of this invention will become apparent from the following description taken in connection with the accompanying drawings, wherein is set forth by way of illustration and example, an embodiment of this invention.

DETAILED DESCRIPTION

Figure 2:
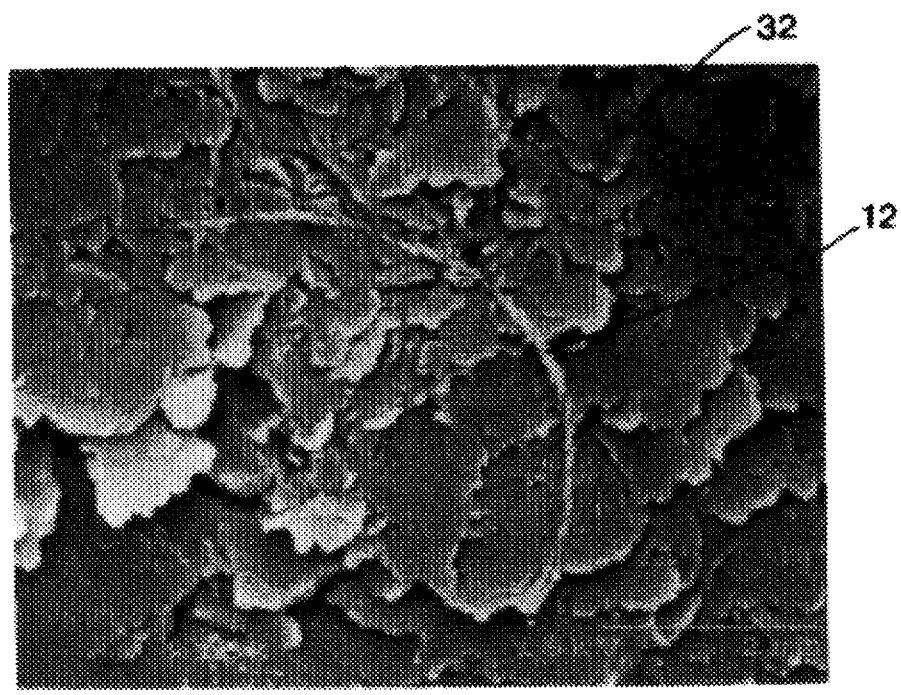
FIG. 2 shows a soap fiber extracted using the method in accordance with the present invention at 15,000 times magnification.

A method of separating and isolating individual soap fibers, which typically comprise the solid component of a metallic grease, from the liquid component of the grease is disposed. FIG. 2 shows an image, obtained by electron microscopy, of a lithium soap fiber 12 isolated in accordance with the present method and magnified 15,000 times. It should be appreciated that the capability of isolating and imaging individual soap fibers allows the fibers to be studied microscopically for analysis of their features, such as morphology, diameter, length, etc. Such information is helpful in quantifying the milling process used in making grease to assure that the grease will consistently have the proper lubricating properties.

In the present invention a sample of grease to be analyzed is admixed with a suitable solvent to remove the liquid phase component of the grease, typically oil, from the soap fibers and provide a final liquid product having the soap fibers therein. The grease may comprise a metallic soap grease such as aluminum, lithium, calcium or sodium grease, or a lithium complex, aluminum complex, calcium complex or barium complex grease. The solvent employed may be selected from any organic solvent capable of dissolving the oil and thus removing the liquid phase component from the fibers.

Figure 1:
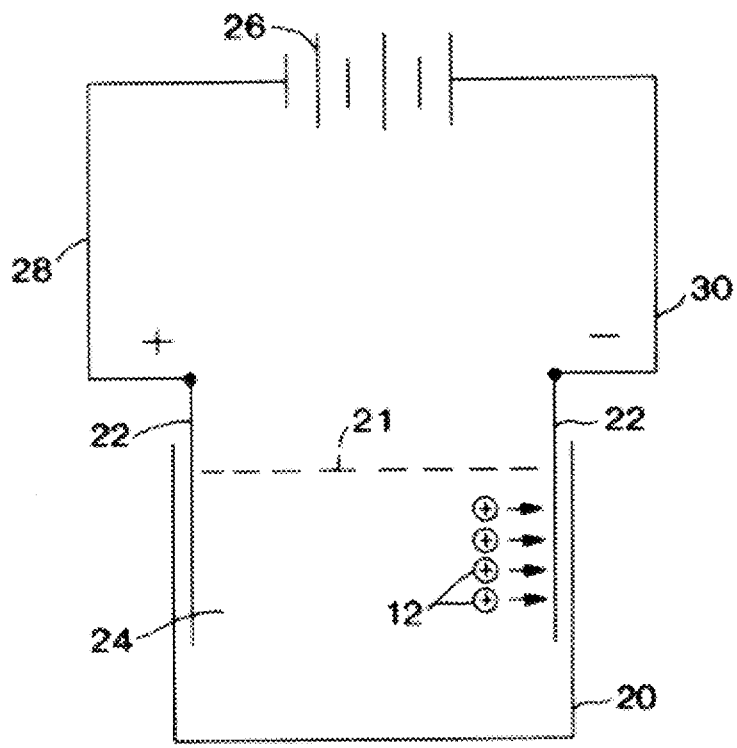
FIG. 1 is a schematic diagram illustrating the extraction of soap fibers in accordance with the present invention.

By way of a specific example of the practice of the present method, the soap fibers in lithium grease or lithium complex greases are extracted from the oil by using hexane as the solvent pursuant to the following procedure. Approximately ¼ gram of the grease is added to 50 milliliters of hexane in a vessel such as a glass beaker 20 (FIG. 1). Either a 100 ml or a 250 ml beaker is suitable. If necessary, the admixture may be gently agitated with back and forth motion to facilitate dissolving the grease, and then allowed to settle for approximately 8–12 hours. After settling, approximately 40 ml of the hexane is removed from the beaker without disturbing the residue of fibers which have settled to the bottom of the beaker 20. The liquid volume within the beaker is increased again to 50 milliliters with the addition of hexane and again allowed to settle. This step may be repeated several times to facilitate the complete removal of the oil from the fibers. Upon completely removing the oil from the soap fibers, fresh hexane is added to increase the volume to 100 ml as represented by the level 21. Thus, a final hexane/soap fiber suspension 24 for separating the soap fibers from one another is obtained.

The final suspension 24 is in contact with a pair of spaced electrodes provided in the beaker 20, which may be formed by attaching two strips of aluminum foil 22, each approximately one inch wide and four inches long, to opposite interior sides of the glass beaker 20. This is easily accomplished by folding one end of each aluminum foil strip 22 over the top rim of the beaker 20 so that each strip 22 extends downwardly along the inside surface of the beaker 20. The foil strips 22 must be long enough to extend into the hexane/fiber suspension 24 beneath liquid level 21. A conductive material other than aluminum foil may be substituted therefor. Also, a separate vessel containing the electrodes 22 may be provided and the hexane/fiber suspension 24 transferred into it.

After the final suspension 24 is prepared, it is gently agitated and allowed to settle until the cloudiness settles to the bottom of the suspension. The electrodes 22 are then connected to positive and negative leads 28 and 30 from a DC power source such as a battery 26. The electromotive force thereby applied charges the left electrode 22 positive and the right electrode 22 negative (FIG. 1). The minimum applied voltage is approximately nine volts with 12 volts being preferable. The suspension 24 is allowed to set with the voltage applied thereto for a predetermined energization period, preferably approximately five minutes. Thereafter, a small quantity of the suspension 24 is withdrawn from the beaker 20 for analysis by partially submersing a micropipette into the suspension in a region proximate the negative electrode 22, e.g., approximately five millimeters from the negative electrode.

Figure 3:
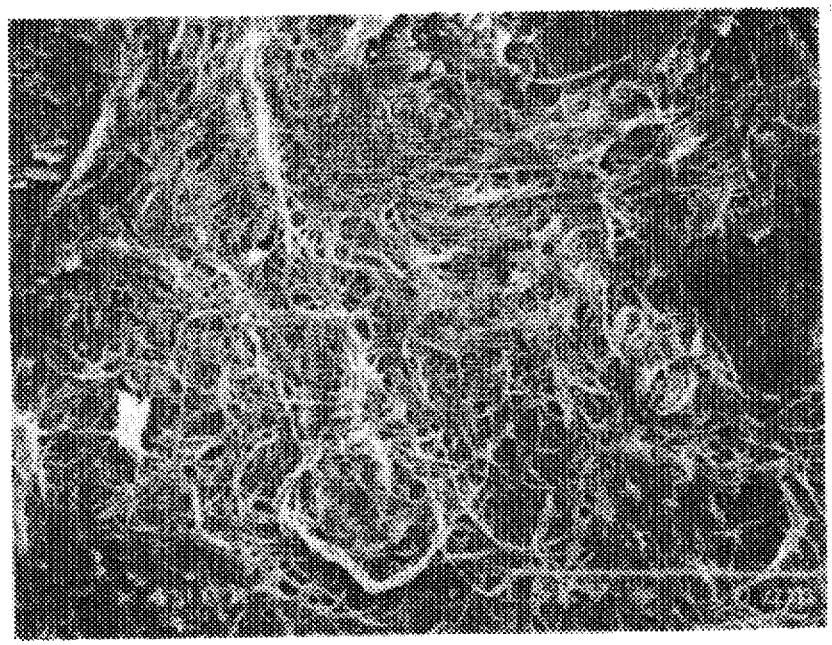
FIG. 3 shows a tangled mass of soap fibers as extracted from grease using a prior method of separation at 4,000 times magnification.
Figure 4:
FIG. 4 shows a tangled mass of soap fibers as extracted from grease using a prior method of separation at 10,000 times magnification.

Because the soap fibers 12 are positively charged, they separate from one another when the voltage is applied to the positive and negative electrodes 22 and migrate toward the negatively charged electrode as illustrated in FIG. 1. The rate at which the fibers 12 move toward the negative electrode 22 is dependent upon the voltage applied. It is believed that collection of individual fibers 12, as in FIG. 2, as opposed to fiber masses, as in FIGS. 3 and 4, is dependent not only upon the attraction to the negative electrode but also on the individual fibers 12 moving toward the negative electrode more readily due to their smaller size.

The withdrawn quantity of suspension 24 within the micropipette is deposited onto a conductive support, preferably a polished carbon stub, as is conventional in electron microscopy. A portion of the surface 32 of the stub is seen magnified 15,000 times in FIG. 2. The hexane is allowed to evaporate, leaving the dry fibers on the stub which is then coated with gold (Au) in a sputter coating device for 30 seconds at 20 milliamperes of current. The gold coating makes the surface 32 more conductive and enhances imaging and the emission of secondary electrons.

Analysis of the fibers as mounted on the stub is completed with the use of a variable pressure scanning electron microscope (such as Hitachi S-2460N) integrated with an image and X-ray microanalysis computer system. The microanalysis system (for example, Voyager III by Noran Instruments) makes it possible to measure distances, areas, inclusions and other relevant data with a great degree of accuracy with respect to the separated fibers 12. The separation technique of the present invention allows the technician to image the fibers individually, as seen in FIG. 2 where the single lithium soap fiber 12 appears alone against background clutter caused by irregularities in the surface 32 of the carbon stub detectible at 15,000× magnification. This is in contrast to prior separation methods where the fibers were tangled, making measurements and accurate analysis difficult. See FIGS. 3 and 4.

It is to be understood that while certain forms of this invention have been illustrated and described, it is not limited thereto except insofar as such limitations are included in the following claims and allowable equivalents thereof.

Having thus described the invention, what is claimed as new and desired to be secured by Letters Patent is as follows:

1. A method of separating soap fibers from the liquid phase component of grease to prepare the fibers for microscopic analysis, said method comprising the steps of:
   (a) admixing a sample of the grease with a solvent to remove the liquid phase component from the fibers and provide a final liquid product having said fibers therein;
   (b) contacting said final product with a pair of spaced electrodes;
   (c) applying an electromotive force to said electrodes to charge the same positive and negative respectively; and
   (d) withdrawing for analysis a small quantity of said final product from a region thereof proximate the negative electrode, after said electromotive force has been applied for a predetermined period of time.

2. The method as claimed in claim 1 and further comprising the additional step of depositing the withdrawn quantity on a support for microscopic viewing after evaporation of the solvent.

3. The method as claimed in claim 1, wherein said step (a) includes diluting the admixture with repeated amounts of said solvent until said final product is essentially free of said liquid phase component.

4. The method as claimed in claim 1, wherein said step (c) includes applying a direct voltage across said electrodes.

5. The method as claimed in claim 4, wherein said voltage is at least approximately nine volts.

6. The method as claimed in claim 1, wherein said predetermined period of time is at least approximately five minutes.

7. A method of separating soap fibers from the liquid phase component of grease to prepare the fibers for microscopic analysis, said method comprising the steps of:
   (a) admixing a sample of the grease with a solvent to remove the liquid phase component from the fibers, and repeatedly diluting the admixture with additional amounts of said solvent to provide a final liquid product which is essentially free of said liquid phase component and has said fibers in suspension therein;
   (b) introducing said final product to a vessel containing a pair of spaced electrodes;
   (c) applying an electromotive force to said electrodes to charge the same positive and negative respectively and cause a direct current to flow in the final product;
   (d) withdrawing a small quantity of said final product from a region thereof proximate the negative electrode, after said electromotive force has been applied for a predetermined period of time; and
   (e) depositing the withdrawn quantity on a conductive support for viewing by an electron microscope after evaporation of the solvent.

* * * * *